United States Patent [19]
Sun

[11] Patent Number: 6,001,646
[45] Date of Patent: *Dec. 14, 1999

[54] METHOD AND VECTOR FOR EXPRESSION AND ISOLATION OF BIOLOGICALLY ACTIVE MOLECULES IN URINE

[75] Inventor: Tung-Tien Sun, Scarsdale, N.Y.

[73] Assignee: New York University, New York, N.Y.

[*] Notice: This patent is subject to a terminal disclaimer.

[21] Appl. No.: 08/907,800

[22] Filed: Aug. 8, 1997

Related U.S. Application Data

[63] Continuation-in-part of application No. 08/464,961, Jun. 5, 1995, Pat. No. 5,824,543.

[51] Int. Cl.⁶ ............................. C12N 15/63; C07H 21/04
[52] U.S. Cl. ...................... 435/320.1; 536/23.5; 536/24.1
[58] Field of Search ................................. 435/69.1, 91.4, 435/320.1, 91.6; 536/23.1, 24.1, 23.5

[56] References Cited

U.S. PATENT DOCUMENTS 4,873,191  10/1989  Wagner et al. ............................ 800/25

OTHER PUBLICATIONS

Jaenisch et al., "Chromosomal Position and Activation of Retroviral Genomes Inserted into the Germ Line of Mice", *Cell* 1981, 24, 519.

Koss, L.G. "The Asymmetric Unit Membranes of the Epithelium of the Urinary Bladder of the Rat", *Lab. Invest.* 1969, 21, 154–168.

Lin et al. "Precursor Sequence Processing, and Urothelium-specific Expression of a Major 15–kDa Protein Subunit of Asymmetric Unit Membrane", *J. Biol. Chem.* 1994, 269, 1775–1784.

Mercer et al. "The Dopamine β–Hydroxylase Gene Promoter Directs Expression of *E. coli* lacZ to Sympathetic and Other Neurons in Adult Transgenic Mice", *Neuron* 1991, 7, 703–716.

Perucho et al., "Genetic and Physical Linkage of Exogenous Sequences in Transformed Cells", *Cell* 1980, 22, 9–17.

Peschon et al. "Spermatid–specific expression of protamine 1 in transgenic mice", *Proc. Natl. Acad. Sci. USA* 1987, 84, 5316–5319.

Ryan et al. "Chromosomal localization of uroplakin genes of cattle and mice", *Mamm. Genome* 1993, 4, 656–661.

Soriano et al. "Tissue–Specific and Ectopic Expression of Genes Introduced into Transgenic Mice by Retroviruses", *Science* 1986, 234, 1409–1413.

Stewart et al. "Expression of retroviral vectores in transgenic mice obtained by embryo infection", *Embo. J.* 1987, 6, 383–388.

Staehelin, L.A. "Lumenal Plasma Membrane of the Urinary Bladder", *J. Cell Biol.* 1972, 53, 73–91.

Wu et al. "Large Scale Purification and Immunolocalization of Bovine Uroplakins I, II, and III", *J. Biol. Chem.* 1990, 265, 19170–19179.

Wu et al. "Uroplakins Ia and Ib, Two Major Differentiation Products of Bladder Epithelium, Belong to a Family of Four Transmembrane Domain (4TM) Proteins", *J. Biol. Chem.* 1994, 269, 13716–13724.

Wu, X. –R. and Sun, T. –T. "Molecular cloning of a 47 kDa tissue–specific and differentiation–dependent urothelial cell surface glycoprotein", *J. Cell Sci.* 1993, 106, 31–43.

Yu et al., "Uroplakin I: A 27–kD Protein Associated with the Assymmetric Unit Membrane of Mammalian Urothelium", *J. Cell Biol.* 1990, 111, 1207–1216.

Yu et al., "Identification of an 85–100 kDa Glycoprotein as a Cell Surface Marker for an Advanced Stage of Urothelial Differentiation: Association with the Inter–plaque ('Hinge') Area", *Epithelial Cell Biol.* 1992, 1, 4–12.

Yu, J. "Uroplakin I: A 27–kD Protein Associated with the Asymmetric Unit Membrane of Mammalian Urothelium", *J. Cell Biol.* 1994, 125, 171–182.

Line et al. A tissue–specific promoter that can drive a foreigh gene to express in the suprabasal urothelial cells of transgenic mice. PNAS (USA) vol. 92:679–683, Jan. 1995.

*Primary Examiner*—Nancy Degen
*Assistant Examiner*—William Sandals
*Attorney, Agent, or Firm*—Browdy and Neimark

[57] ABSTRACT

A vector is provided which contains a promoter construct linked to a heterologous gene encoding a selected biologically active molecule wherein the promoter construct is capable of directing urothelial expression of the heterologous gene. Methods of isolating biologically active molecules from urine of animals transfected with this vector and transgenic animals containing this vector are also provided.

1 Claim, 5 Drawing Sheets

METHOD AND VECTOR FOR EXPRESSION AND ISOLATION OF BIOLOGICALLY ACTIVE MOLECULES IN URINE

The instant application is a continuation-in-part of U.S. application Ser. No. 08/464,961 filed Jun. 5, 1995 now U.S. Pat. No. 5,824,543.

BACKGROUND OF THE INVENTION

Methods of producing biologically active molecules by transfer of recombinant genes into cell in culture and into live animals have been developed. For example, DNA molecules have been introduced into cultured cells by calcium phosphate precipitation or electroporations. Graham and Van der Ebb *Virology* 1973, 52, 456–467; Perucho et al. *Cell* 1980, 22, 9–17; Chu et al. *Nucleic Acids Research* 1987, 15, 1311–1326; and Bishop and Smith *Molecular Biology Medicine* 1989, 6, 283–298. DNA molecules have also been introduced into the nucleus of cells in culture by direct microinjection. Gordon et al. *Proc. Natl Acad. Sci. USA* 1980, 77, 7380–7384; Gordon and Ruttel *Methods in Enzymology* 1983, 101, 411–433; and U.S. Pat. No. 4,873,191.

However, there are two major problems of producing biologically active molecules such as protein products on a commercially viable scale via these methods. First, bacterial expression systems frequently fail to modify the proteins properly, i.e., by glycosylation, etc. Second, the subsequent isolation of gene products from the expression systems can be extremely difficult. In bacteria, yeast, and baculovirus systems the expressed proteins are most often purified from insoluble intracellular compartments. Secreted proteins in yeast require specialized protease-deficient strains coupled with appropriate vectors with secretion signals.

Retroviral vectors have also been used to introduce DNA molecules into the genome of animals. Jaenisch et al. *Cell* 1981, 24, 519; Soriano et al. *Science* 1986, 234, 1409–1413; and Stewart et al. *Embo. J*. 1987, 6, 383–388. Recombinant genes have been introduced into primary cultures of bone marrow, skin, fibroblasts, or hepatic or pancreatic cells and then transplanted into live animals. There has also been success in using mammary gland-specific promoters to drive the expression of foreign proteins in these secretory glands, ultimately leading to their secretion in the resultant milk. This method has been used commercially to express human growth hormone in cows and sheep. WO 94/05782. The copious volumes of milk produced by cows and sheep make this procedure attractive. However, this method suffers from several potential drawbacks: one being that the expressed protein even at relatively high levels must be purified away from a large amount of milk proteins such as caseins, immunoglobins, lactoferrins which may also entrap the desired valuable product; another being that certain protein products may be insoluble in the calcium-rich environment of milk fluid; and another being that this method requires the use of pregnant animals which are expensive and time consuming to produce.

SUMMARY OF THE INVENTION

An object of the present invention is to provide a vector comprising a promoter construct capable of directing urothelial gene expression of a heterologous gene encoding a selected biologically active molecule linked thereto. The vectors of the present invention are useful in directing the expression of the heterologous gene in urothelial cells transfected with the vector which then secrete the encoded gene product into the urine for isolation, thus transforming the bladder into a bioreactor.

Accordingly, another object of the present invention is to provide a method of producing a selected biologically active molecule in urine of an animal wherein urothelial cells in the animal are transfected with the vector so that the heterologous gene of the DNA sequence is expressed and the selected biologically active molecule is recovered in urine produced by the animal.

Another object of the present invention is to provide nonhuman transgenic animals produced using this vector.

BRIEF DESCRIPTION OF THE FIGURES

FIGS. 1a and 1b show the organization and nucleotide sequence of the mouse uroplakin II (UPII) genomic DNA. FIG. 1a provides the exon-intron organization of mouse UPII gene. The open and filled thick boxes denote the five coding sequences (exons) and non-coding sequences (introns), respectively, of the gene. The open and filled thin boxes represent a $(CA)_n$ dinucleotide repeat region and an Alu-like murine B1 repeat, respectively. G1 and G2 designate two independent and partially overlapping genomic clones. The restriction sites are SacI (S), NcoI (N), BamHI (B), SalI (Sal), and XhoI (X). FIG. 1b provides the nucleotide sequence (SEQ ID NO: 1) of a 4-kb SacI fragment of mouse UPII gene. A reversed B1 repetitive sequence (in the 5' upstream region) and a potential polyadenylation site (AATAAA; in the 3' untranslated region) are underlined and double-underlined, respectively. The wavy arrow denotes the transcriptional initiation site. Broken arrows marked 1 to 4 denote the intron/exon junctions of the four introns. The predicted first amino acid residue of mature UPII protein sequence is marked with an asterisk (SEQ ID NO: 2). The preceding domain contains a pre and a pro sequence of 25 and 59 amino acids, respectively. The complete amino acid sequence shown in FIG. 1(b) is SEQ ID NO:2.

FIG. 3a provides a restriction map (abbreviations as described in FIG. 1) of the endogenous murine UPII gene. A 500-bp PCR fragment (thick bar) was used as a probe which detects a 1.4-kb NcoI fragment of the endogenous UPII genome but a shorter 1.1-kb NcoI fragment of the transgene. FIG. 3b provides a restriction map of the transgene. A 3.6-kb 5'-flanking sequence of the UPII gene was inserted into an *Escherichia coli* β-galactosidase (β-gal)-encoding placF vector. In this particular test expression vector, a sequence containing a part of exon 1 and all of intron 1 and exon 2 of the mouse protamine-1 gene (mp1) was placed at the 3'-end of the β-gal (or lacZ) gene to provide an exon/intron splicing site and a polyadenylation signal. This chimeric gene was cut out from the vector, gel-purified, and microinjected into mouse eggs.

DETAILED DESCRIPTION OF THE INVENTION

Figure 1A:
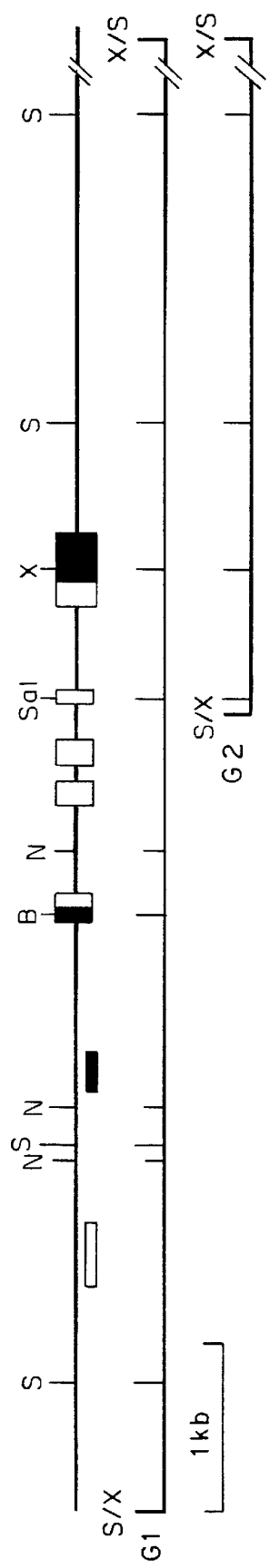

Urine in the bladder is of relatively high osmolality (50 to 1,000 mosmol/kg), with pH values as low as 4.5 and high concentrations of urea and ammonium. The lumen of the bladder therefore provides an advantageous environment for the production of proteins that are normally difficult to express due to insolubility. The urea and high osmolality may serve as in situ denaturants and chaotropic agents. However, urine contains relatively little protein, in comparison with milk, as the kidneys are designed to prevent protein loss, therefore urothelial promoter-driven expression of proteins which by-passes the kidney produces the desired protein in a solution with relatively little contaminating host endogenous proteins.

In the present invention, a vector and method have been developed for expressing biologically active molecules in the luminal cavity of the bladder of transgenic mammals.

The vector of the present invention comprises a promoter construct capable of directing urothelial gene expression of a heterologous gene encoding a selected biologically active molecule linked to the promoter construct. Promoters active in directing expression in the urothelium can be routinely identified in accordance with the teachings provided herein and used in the promoter construct of the vectors of the present invention.

Urothelium, also known as transitional epithelium, is a multilayered epithelium that covers the surface of much of the urogenital tract including the renal pelvis, ureter, the entire bladder and a portion of the urethra. The apical surface of urothelium, in direct contact with the urine, is covered with numerous rigid looking plaques. These plaques cover a large portion of the apical surface of mammalian urothelium. Hicks, R. M. *J. Cell Biol.* 1965, 26, 25–48; Koss, L. G. *Lab. Invest.* 1969, 21, 154–168; Staehelin, L. A. *J. Cell Biol.* 1972, 53, 73–91. They are believed to play a crucial role as a permeability barrier (Hicks, R. M. *Biol. Rev.* 1975, 50, 215–246) and/or as physical stabilizer of the urothelial cell surface (Staehelin, L. A. *J. Cell Biol.* 1972, 53, 73–91). When viewed in cross section, the outer leaflet of the plaque is almost twice as thick as the inner one, hence the term "asymmetrical unit membrane" or "AUM" has been used to describe these plaques.

It has recently been shown that AUM contain 4 major integral membrane proteins which are called uroplakin Ia (UPIa; 28 kDa), uroplakin Ib (UPIb; ~27 kDa), uroplakin II (UPII; 15 kDa) and uroplakin III (UPIII; 47 kDa) EM-immunolocalization studies established that these uroplakins are AUM-associated in situ, thus establishing them as the major protein subunits of urothelial plaques. Yu et al. *J. Cell Biol.* 1990, 111, 1207–1216; Wu et al. *J. Biol. Chem.* 1990, 265, 19170–19179. Immunohistochemical survey of various bovine tissues established that these UPs are urothelium-specific being present in the upper cell layers of the urothelia that cover the urogenital tract including the renal pelvis, ureter, bladder and part of the urethra. These data established uroplakins as excellent markers for an advanced stage of urothelia differentiation. Yu et al. *J. Cell Biol.* 1990, 111, 1207–1216; Wu et al. *J. Biol. Chem.* 1990, 265, 19170–19179. Furthermore, uroplakins Ia, Ib, II and III appear to be the major protein components of all mammalian urothelial plaques. They are found in eight other mammalian species (human, monkey, sheep, pig, dog, rabbit, rat, and mouse), and the AUMs of these species appear morphologically similar, bearing crystalline patches of 12-nm protein particles with a center-to-center spacing of 16.5 nm. Wu et al. *J. Biol. Chem.* 1994, 269, 13716–13724.

The primary structures of UPs have recently been elucidated by cDNA cloning. The results established the existence of two closely related UPI isoforms, the 27-kDa UPIa and the 28-kDa UPIb. Yu, J. *J. Cell Biol.* 1994, 125, 171–182. The mRNAs of all four known UPs have recently been shown to be urothelium-specific, indicating that expression of UP genes is transcriptionally regulated. Yu, J. *J. Cell Biol.* 1994, 125, 171–182; Lin et al. *J. Biol. Chem.* 1994, 269, 1775–1784; Wu, X.-R. and Sun, T.-T. *J. Cell Sci.* 1993, 106, 31–43.

The expression of the mouse UPII gene, like its bovine counterpart, is urothelium- and late-differentiation stage-specific. Using transgenic mouse techniques, a 3.6-kb 5' flanking region has now been identified as a promoter comprising the cis-elements for directing the expression of a heterologous reporter gene specifically and efficiently to the suprabasal cell layers of the urothelium in a manner similar to the endogenous UPII gene. Using this promoter, it has now been found that foreign proteins can be directed to the upper cell layers of the bladder urothelium for expression and secretion into urine.

Figure 1B-1:
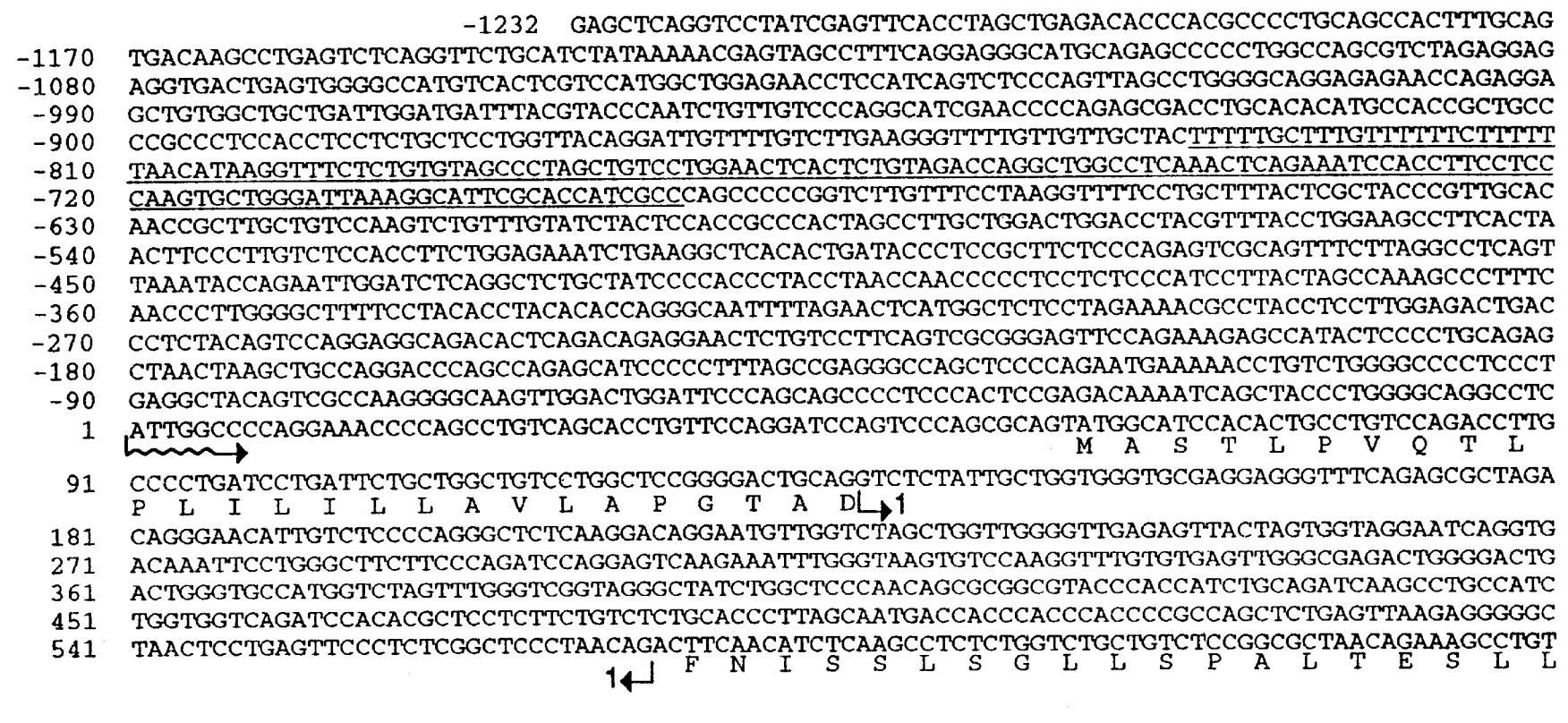
Figure 1B-2:
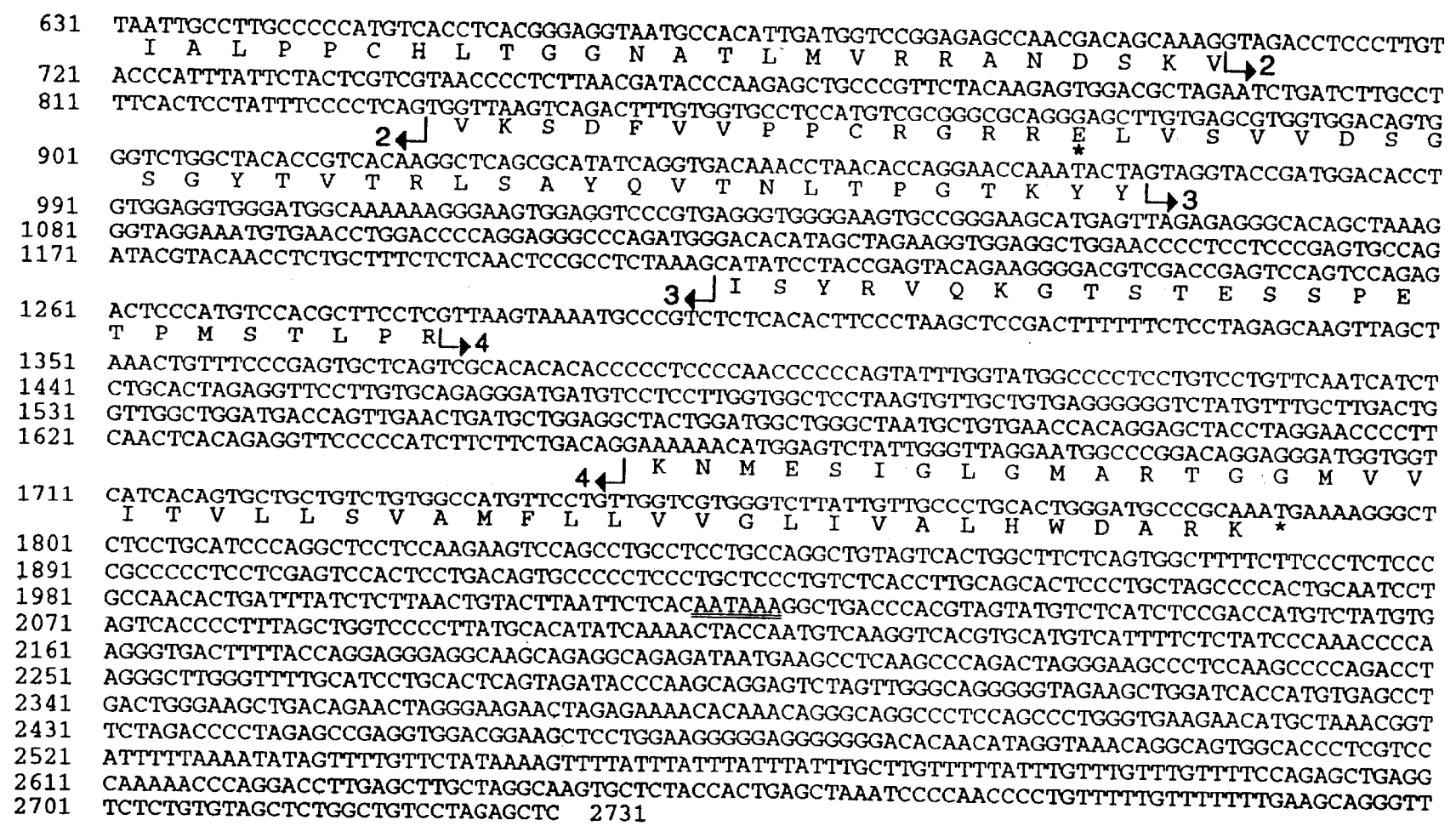

Using a bovine UPII cDNA as a probe, a 16-kb mouse genomic clone (G1) was isolated which contains an ~2.5-kb transcribed region that is flanked by ~3.5-kb and ~10 kb of 5'-and 3'-sequences, respectively (see FIG. 1a). Alignment of the coding sequence with the UPII cDNA sequences of cattle (Lin et al. *J. Biol. Chem.* 1994, 269, 1775–1784), which are highly homologous, defined the exon/intron junctions of four introns (FIG. 1b). 5'-RACE (Frohman et al. *Proc. Nat'l Acad. Sci. USA* 1988, 85, 8998–9002) experiments using mouse bladder mucosal mRNA as a template established that the transcription site of the UPII gene is located at 60-bp 5'-upstream of the translation initiation codon and 27-bp downstream of a putative TATA box. The 5'-upstream region contains an Alu-like B1 repetitive sequence (−830 bp) and a $(CA)_n$ stretch (~−2.1 kb). Finally, a polyadenylation signal resides ~230 bp downstream of the translation stop codon (see FIG. 1b).

Figure 2:
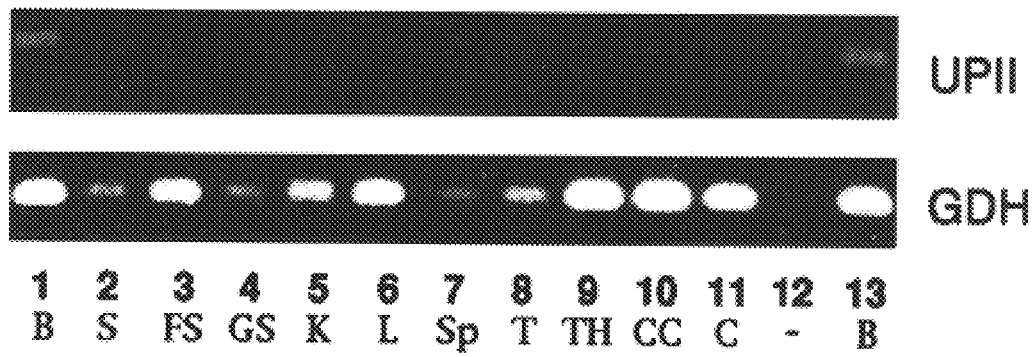
FIG. 2 illustrates the tissue distribution of UPII mRNA as assayed by RT-PCR. Poly(A)+mRNAs (0.3–0.4 mg) from mouse bladder (lanes 1 and 13), skin (2), forestomach (3), glandular stomach (4), kidney (without renal pelvis) (5), liver (6), spleen (7), testis (8), and thalamus/hypothalamus (9), cerebral cortex (10), and cerebellum (11) regions of the brain were reverse-transcribed, and amplified with either UPII-specific primers (Upper; 266 bp) or glyceraldehyde-3-phosphate dehydrogenase (GDH)-specific primers (Lower, as an internal control for comparison; 130 bp). The PCR products were then electrophoresed on a 1.3% agarose gel and stained with ethidium bromide. Lane 12 is a negative control (no cDNA template). The 266-bp UPII product was detected in abundance in bladder, but not in any other tested tissues, including the hypothalamus.

The mouse UPII gene is also expressed in the urothelium. mRNAs were prepared from various mouse tissues and probed for the presence of UPII sequences by reverse transcription-polymerase chain reaction (RT-PCR) assay. A large amount of UPII product of expected size (266-bp) was generated from the bladder, but not from skin, forestomach, glandular stomach, kidney, liver, spleen, testis, or the hypothalamus/thalamus cortex and cerebellum of the brain (see FIG. 2).

A rabbit antiserum previously prepared against a synthetic peptide corresponding to the N-terminal amino acid sequence ELVSVVDSGSG (1–11) (a.a 85–95 of SEQ ID NO: 2) of mature bovine UPII (Lin et al. *J. Biol. Chem.* 1994, 269, 1775–1784) immunohistochemically stains the 15-kDa bovine UPII and localizes it to the superficial cell layers of bovine urothelium. This antiserum cross-reacted well with mouse UPII, which contains an identical epitope, but migrates slightly slower at an apparent 17 kDa mass. Immunofluorescent staining of frozen sections of mouse bladders showed that the UPII was associated with the all the suprabasal cell layers, suggesting that the onset of UPII gene expression in mouse was earlier than that in cattle.

Figure 3A:
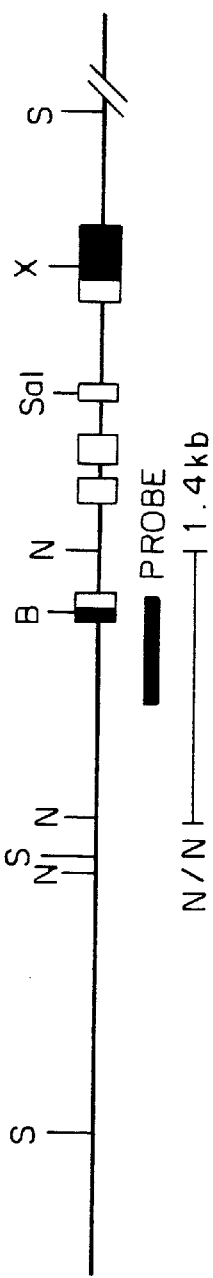
FIGS. 3a and 3b illustrate the construction and quantitation of a representative transgene.
Figure 3B:
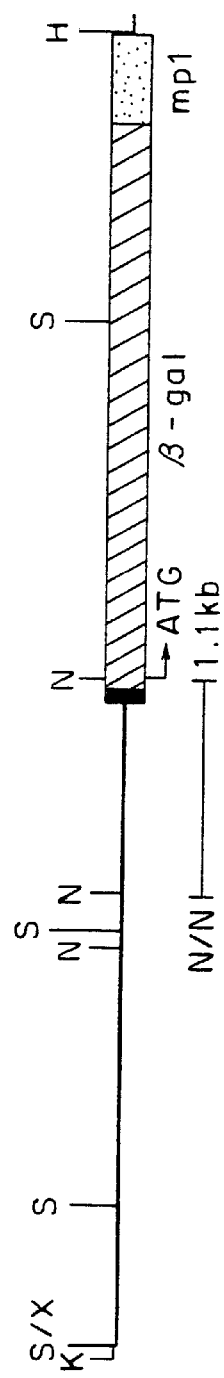

To define the cis promoter elements for urothelial-specific expression and to demonstrate that heterologous genes can be targeted to the suprabasal urothelial cells as endogenous UPII, a transgenic mouse was constructed that contains a chimeric gene in which a lacZ reporter gene was under the regulation of a 3.6-kb 5'-flanking sequence of the mouse UPII gene (FIG. 3b). The DNA construct was injected into fertilized mouse eggs for transgenic mouse production. Southern blot analyses of the tail DNAs showed that the transgene was integrated into the genomes of 4 of 25 mice. Three of these animals transmitted the reporter gene into their progeny. Southern blot analyses established that the genomic DNAs of these three transgenic lines, TG1, TC2, and TG3, contained roughly 40, 6, and 30 copies, respectively, of the reporter gene per diploid genome. Probing the same Southern blot with the lacZ sequence showed that the transgenes of all three lines were in tandem repeats and were integrated into independent sites.

In all three mice lines, the transgene was expressed in the suprabasal cells of the bladder epithelium in an expression pattern similar to the endogenous UPII gene. The staining correlated somewhat with gene dosage, as it was intense in TG1 (40 copies) but moderate in TG2 (6 copies) and TG3 (30 copies). β-galactosidase activity was only observed in the bladder and other urothelia of mice that had inherited the transgene, confirming that the activity was transgene-specific. In all three transgenic mice, no β-galactosidase activity was detected in any of the non-urothelial stratified epithelia tested, including those of the skin, tongue, cornea, esophagus, and forestomach. The reporter gene product was also undetectable in all other epithelia tested, including those of liver, lung, glandular stomach, small and large intestine, uterus, and testis; or mesenchymal tissues, including fibroblasts, endothelial cells, spleen, and various muscle cells.

Experiments have also been performed wherein uroplakin II promoter was used to drive the expression of the biologically active human growth hormone gene in the urothelium of transgenic mice. In these experiments, a vector was constructed with the 3.6-kb UPII promoter placed upstream from a human growth hormone cDNA. The vector was then injected into the fertilized mouse eggs for transgenic mouse production. Thirteen founder mice were generated. Of these, six (5 male and 1 female) transmitted the transgene to their offspring. Immunofluorescence staining of the bladder epithelium of these transgenic mice using antibodies to hGH showed strong staining indicating high level of expression. Immunolocalization performed by high resolution electron microscopy showed the accumulation of electron dense, aggregates of hGH that are labeled by immuno-gold particles conjugated with antibodies to hGH. Most of the hGH particles are found in the vesicles lined with the asymmetrical unit membrane that are normally involved in transporting the uroplakins to the apical surface of the bladder epithelium. In addition, some of the hGH particles formed another distinct population of cytoplasmic vesicles thus revealing the presence of a previously unrecognized secretory pathway that may normally operate at a low level in bladder epithelium. The high level of overexpression of hGH makes these vesicles easily visible.

Urine from these mice was collected and hormone levels determined by radioimmunoassay. Many of the F1 offspring had a significant levels of the human growth hormone in their urine (up to 300 ng/ml) thus demonstrating that the biologically active molecule was secreted into the urine. Further, blood concentrations of the hormone were less than 5 ng/ml indicating that the synthesized hormone is secreted vectorially into the bladder cavity rather than into the bloodstream.

Other urothelia closely related to the epithelium of the bladder known to cover other areas of the urinary tract, such as the renal pelvis of the kidney, the ureter, and the urethra and which also elaborate AUM plaques, exhibit similar expression of the transgene.

These data show that a promoter active in directing expression in the urothelium of an animal, such as the 3.6-kb 5'-flanking sequence of the mouse UPII gene, can drive both a heterologous reporter gene and a gene for a biologically active molecule to express in the upper cell layers of the bladder epithelium. The lack of expression in non-urothelial tissues indicates a high degree of tissue-specificity and demonstrates that the cis elements of this promoter region provide very tight regulatory control on tissue-specific and differentiation-dependent expression of a gene placed downstream of the promoter. As these results were corroborated in independent transgenic lines with differing sites of transgene integration, they show that the inherent promoter activity is responsible for the tissue-specific expression and is not due to the effect of neighboring sequences of the transgene integration sites. This tight regulation is a very desirable property of any promoter used for production of foreign protein products in host transgenic animals, as it assures correct delivery to target production sites, high efficiency of expression of transduced genes, and minimizes toxic effect of aberrant expression.

While these experiments were conducted using the mouse UPII promoter, as will be obvious to those of skill in the art upon this disclosure, other promoter constructs capable of directing urothelial gene expression can used to yield similar results. For example, mouse uroplakin II 5'-upstream sequences that are shorter or longer than 3.6-kb but can still achieve the same degree of urothelium expression. Also useful are DNA sequences with relatively minor modifications to the mouse UPII promoter, such as sequences with point mutations, partial deletions or chemical modifications.

In addition, sequences that are related to the 3.6 kb 5' flanking sequence of the mouse uroplakin gene, including, but not limited to, promoter sequences of uroplakin-II-homologous genes of other mammalian species such as human, cattle, sheep, goat, rabbit and rat, can also be used. There is sufficient similarity between this gene in different species, so that similar results with the UPII promoter sequence in other animals is expected. For example, the UP gene organization (Ryan et al. *Mamm. Genome* 1993, 4, 656–661), cDNA (Lin et al. *J. Biol. Chem.* 1994, 269, 1775–1784) and protein sequences, tissue patterns of expression, and morphology of AUMs are strikingly similar between the mouse and cow. The amino acid sequence of bovine and mouse UPII are highly similar, sharing 84 of their 100 amino acid residues. Wu et al. *J. Biol. Chem.* 1994, 269, 13716–13724. In addition, although the onset of expression of the UPII gene is different in these two species, UPII is clearly differentiation-related in both cow and mouse urothelia.

Further, promoters of other genes that are active in directing expression in the urothelium are known and can also be used in the vectors of the present invention. Examples include, but are not limited to, the promoter of uroplakin 1a (Yu et al. *J. Cell Biol.* 1994, 125, 171–182; Yu et al. *J. Cell Biol.* 1990, 111:1207–16), uroplakin Ib (Yu et al. *J. Cell Biol.* 1994, 125, 171–182; Yu et al. *J. Cell Biol.* 1990, 111:1207–16), uroplakin III (Wu, X. R., and Sun, T. T. *J. of Cell Science* 1993, 106, 31–43, and the urohingin gene (Yu et al. *Epithelial Cell Biol.* 1992, 1, 4–12).

Identification of additional promoters active in directing gene expression in the urothelium is performed routinely using the subtraction library technique. Using this technique which eliminates the cDNAs that are shared by multiple tissues (Diatchenko et al. *Proc. Nat'l Acad. Sci.* 1996, 93, 6025–6030), a library highly enriched in bladder specific cDNAs was generated. Total RNAs were isolated from bovine bladder, kidney, lung, spleen, muscle, esophagus, stomach, intestine, colon, liver and brain. Northern blot analysis of these mRNAs using an actin cDNA as a probe demonstrated the intactness of the acting mRNA in all of these preparations. Bladder cDNAs were then used as the "tester", and the cDNAs of all the other non-bladder tissues, referred to as the "drivers" were subtracted from the bladder cDNAs. The cDNAs of the non-subtracted and the subtracted were probed using acting cDNA or uroplakin Ib. The results indicate that the original bovine bladder cDNA preparation contained abundant acting mRNA and relatively little uroplakin Ib mRNA. In contrast, the subtracted library contained almost no detectable acting mRNA (at least 50 fold reduction) but greatly increased uroplakin Ib mRNA (>10 to 15 fold enrichment). Multiple cDNA clones have been isolated from the substraction library and used to probe the mRNAs of various bovine tissues. For example, a uroplakin Ib probe confirmed its bladder specificity. Tissue distribution patterns have also been determined for three unidentified partial cDNAs which are relatively bladder specific. Sequencing data indicate these three clones are novel genes not described previously. It is believed that the promoters of these genes will also be useful in directing expression of a heterologous gene for a biologically active molecule in the urothelium of transgenic animals.

The vectors of the present invention thus transform the bladder into a bioreactor capable of producing a biologically active molecule in the urine for isolation. In one embodiment, this vector is introduced into germ cells to produce a transgenic animal capable of expressing the biologically active molecule in its bladder. As used herein, "biologically active molecule" refers to a molecule capable of causing some effect within an animal, not necessarily within the animal having the transgene. Examples of such molecules include, but are not limited to, adipokinin, adrenocorticotropin, blood clotting factors, chorionic gonadotropin, corticoliberin, corticotropin, cystic fibrosis transmembrane conductance regulators, erythropoietin, folliberin, follitropin, glucagon gonadoliberin, gonadotropin, human growth hormone, hypophysiotropic hormone, insulin, lipotropin, luteinizing hormone-releasing hormone, luteotropin, melanotropin, parathormone, parotin, prolactin, prolactoliberin, prolactostatin, somatoliberin, somatotropin, thyrotropin, tissue-type plasminogen activator, and vasopressin. Of course, as will be obvious to one of skill in the art, the above list is not exhaustive. In addition, new genes for biologically active molecules that will function in the context of the present invention are continually being identified. The biologically active molecule can be isolated from the urine of these transgenic animals. Accordingly, the present invention provides a means for isolating large amounts of biologically active molecules from the urine of transgenic animals which can be used for a variety of different purposes.

In another embodiment, the vector comprises a system which is well received by the urothelial cells lining the lumen of the bladder. An example of a useful vector system is the Myogenic Vector System (Vector Therapeutics Inc. Houston Tex.). In this embodiment, the heterologous gene of the biologically active molecule linked to the promoter construct capable of directing urothelial expression and carried in the vector is introduced into the bladder of an animal in vivo. Introduction of the vector can be carried by a number of different methods routine to those of skill in the art. For example, a vector of the present invention could be placed in direct contact with the urothelium via a rubber urethral catheter or Foley catheter. Vectors of the present invention can also be incorporated into liposomes and introduced into the animal in that form. The transgene is absorbed into one or more epithelial cells capable of expressing and secreting the biologically active molecule into the urine collecting in the bladder. It may be preferred for some biologically active molecules to also engineer a signaling sequence into the vector to insure that the molecule is secreted from the apical surface into the lumen. Use of signaling sequences such as the glycophosphatidylinositol (GPI) linkage in anchoring molecules to a selected surface is well known in the art. The biologically active molecule is then voided from the lumen where it can be collected and separated from other components in the urine.

The following nonlimiting examples are provided to further illustrate the present invention.

EXAMPLES

Example 1

Characterization of the Mouse UPII Gene

A bovine UPII CDNA (Lin et al., *J. Biol. Chem.* 1994, 269, 1775–1784) was used as a probe to screen a mouse EMBL3-SP6A/T7 genomic library (Clontech Laboratories Inc. Palo Alto, Calif.). Two overlapping clones (G1 and G2) were isolated (FIG. 1a) and were sequenced by the dideoxynucleotide termination method. The transcriptional initiation site was determined by sequencing three clones of 5'-RACE (rapid amplification of cDNA ends) products of mouse bladder cDNA.

Example 2

Expression of a Fusion Gene (UPII-lacZ) in Transgenic Mice

A 6-kb XhoI DNA fragment of the G1 genomic clone (FIG. 1a) was subcloned in pGEM7Z and then restriction-cut to yield a 3.6-kb DNA fragment of G1 clone (extending from the XhoI site at −3.6 kb to the BamHI site at −42 bp relative to the transcription initiation site) and inserted into the SmaI site of a lacZ vector, placF, (Peschon et al. *Proc. Natl. Acad. Sci. USA* 1987, 84, 5316–5319; Mercer et al. *Neuron* 1991, 7, 703–716) to generate pUPII-LacZ (FIG. 3). The 7.1-kb fusion gene was excised using Kpn I and Hind III, gel-purified, and microinjected into fertilized mouse eggs (from F1 hybrids of C57BL/6J×DBA2), which were implanted into CD-1 foster mothers. The lacZ transgene was identified by Southern blot analysis of tail DNA in accordance with methods well known in the art. Positive founder animals were back-crossed with (C57BL/6J×DBA2) F1 hybrids to generate semizygous animals that were used for studying transgene expression.

What is claimed is:

1. A vector comprising a promoter construct linked to a heterologous gene encoding a selected biologically active molecule, wherein said promoter construct directs expression of the heterologous gene to the urothelium and is a UP-II promoter.

* * * * *

UNITED STATES PATENT AND TRADEMARK OFFICE
CERTIFICATE OF CORRECTION

PATENT NO. : 6,001,646
DATED : December 14, 1999
INVENTOR(S) : Tung-Tien Sun

It is certified that error appears in the above-identified patent and that said Letters Patent is hereby corrected as shown below:

Column 1,
Line 9, before "Background of the Invention", insert the following new section:
-- GOVERNMENT LICENSE RIGHTS
The U.S. Government has a paid-up license in this invention and the right in limited circumstances to require the patent owner to license others on reasonable terms as provided for by the terms of Contract No. DK039753 and DK049469 awarded by the National Institutes of Health of the U.S. Department of Health and Human Services. --

Signed and Sealed this

Twenty-first Day of June, 2005

JON W. DUDAS
*Director of the United States Patent and Trademark Office*

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 3963 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
GAGCTCAGGT CCTATCGAGT TCACCTAGCT GAGACACCCA CGCCCCTGCA GCCACTTTGC    60
AGTGACAAGC CTGAGTCTCA GGTTCTGCAT CTATAAAAAC GAGTAGCCTT TCAGGAGGGC   120
ATGCAGAGCC CCCTGGCCAG CGTCTAGAGG AGAGGTGACT GAGTGGGGCC ATGTCACTCG   180
TCCATGGCTG GAGAACCTCC ATCAGTCTCC CAGTTAGCCT GGGGCAGGAG AGAACCAGAG   240
GAGCTGTGGC TGCTGATTGG ATGATTTACG TACCCAATCT GTTGTCCCAG GCATCGAACC   300
CCAGAGCGAC CTGCACACAT GCCACCGCTG CCCCGCCCTC CACCTCCTCT GCTCCTGGTT   360
ACAGGATTGT TTTGTCTTGA AGGGTTTTGT TGTTGCTACT TTTTGCTTTG TTTTTTCTTT   420
TTTAACATAA GGTTTCTCTG TGTAGCCCTA GCTGTCCTGG AACTCACTCT GTAGACCAGG   480
CTGGCCTCAA ACTCAGAAAT CCACCTTCCT CCCAAGTGCT GGGATTAAAG GCATTCGCAC   540
CATCGCCCAG CCCCCGGTCT TGTTTCCTAA GGTTTTCCTG CTTTACTCGC TACCCGTTGC   600
ACAACCGCTT GCTGTCCAAG TCTGTTTGTA TCTACTCCAC CGCCCACTAG CCTTGCTGGA   660
CTGGACCTAC GTTTACCTGG AAGCCTTCAC TAACTTCCCT TGTCTCCACC TTCTGGAGAA   720
ATCTGAAGGC TCACACTGAT ACCCTCCGCT TCTCCCAGAG TCGCAGTTTC TTAGGCCTCA   780
GTTAAATACC AGAATTGGAT CTCAGGCTCT GCTATCCCCA CCCTACCTAA CCAACCCCCT   840
CCTCTCCCAT CCTTACTAGC CAAAGCCCTT TCAACCCTTG GGGCTTTTCC TACACCTACA   900
CACCAGGGCA ATTTTAGAAC TCATGGCTCT CCTAGAAAAC GCCTACCTCC TTGGAGACTG   960
ACCCTCTACA GTCCAGGAGG CAGACACTCA GACAGAGGAA CTCTGTCCTT CAGTCGCGGG  1020
AGTTCCAGAA AGAGCCATAC TCCCCTGCAG AGCTAACTAA GCTGCCAGGA CCCAGCCAGA  1080
GCATCCCCCT TTAGCCGAGG GCCAGCTCCC CAGAATGAAA AACCTGTCTG GGGCCCCTCC  1140
CTGAGGCTAC AGTCGCCAAG GGGCAAGTTG GACTGGATTC CCAGCAGCCC CTCCCACTCC  1200
GAGACAAAAT CAGCTACCCT GGGGCAGGCC TCATTGGCCC CAGGAAACCC CAGCCTGTCA  1260
GCACCTGTTC CAGGATCCAG TCCCAGCGCA GTATGGCATC CACACTGCCT GTCCAGACCT  1320
TGCCCCTGAT CCTGATTCTG CTGGCTGTCC TGGCTCCGGG GACTGCAGGT CTCTATTGCT  1380
GGTGGGTGCG AGGAGGGTTT CAGAGCGCTA GACAGGGAAC ATTGTCTCCC CAGGGCTCTC  1440
AAGGACAGGA ATGTTGGTCT AGCTGGTTGG GGTTGAGAGT TACTAGTGGT AGGAATCAGG  1500
TGACAAATTC CTGGGCTTCT TCCCAGATCC AGGAGTCAAG AAATTTGGGT AAGTGTCCAA  1560
GGTTTGTGTG AGTTGGGCGA GACTGGGGAC TGACTGGGTG CCATGGTCTA GTTTGGGTCG  1620
GTAGGGCTAT CTGGCTCCCA ACAGCGCGGC GTACCCACCA TCTGCAGATC AAGCCTGCCA  1680
TCTGGTGGTC AGATCCACAC GCTCCTCTTC TGTCTCTGCA CCCTTAGCAA TGACCACCCA  1740
CCCACCCCGC CAGCTCTGAG TTAAGAGGGG GCTAACTCCT GAGTTCCCTC TCGGCTCCCT  1800
```

```
AACAGACTTC AACATCTCAA GCCTCTCTGG TCTGCTGTCT CCGGCGCTAA CAGAAAGCCT      1860

GTTAATTGCC TTGCCCCCAT GTCACCTCAC GGGAGGTAAT GCCACATTGA TGGTCCGGAG      1920

AGCCAACGAC AGCAAAGGTA GACCTCCCTT GTACCCATTT ATTCTACTCG TCGTAACCCC      1980

TCTTAACGAT ACCCAAGAGC TGCCCGTTCT ACAAGAGTGG ACGCTAGAAT CTGATCTTGC      2040

CTTTCACTCC TATTTCCCCT CAGTGGTTAA GTCAGACTTT GTGGTGCCTC CATGTCGCGG      2100

GCGCAGGGAG CTTGTGAGCG TGGTGGACAG TGGGTCTGGC TACACCGTCA CAAGGCTCAG      2160

CGCATATCAG GTGACAAACC TAACACCAGG AACCAAATAC TAGTAGGTAC CGATGGACAC      2220

CTGTGGAGGT GGGATGGCAA AAAGGGAAG TGGAGGTCCC GTGAGGGTGG GGAAGTGCCG       2280

GGAAGCATGA GTTAGAGAGG GCACAGCTAA AGGGTAGGAA ATGTGAACCT GGACCCCAGG     2340

AGGGCCCAGA TGGGACACAT AGCTAGAAGG TGGAGGCTGG AACCCCTCCT CCCGAGTGCC     2400

AGATACGTAC AACCTCTGCT TTCTCTCAAC TCCGCCTCTA AAGCATATCC TACCGAGTAC     2460

AGAAGGGGAC GTCGACCGAG TCCAGTCCAG AGACTCCCAT GTCCACGCTT CCTCGTTAAG    2520

TAAAATGCCC GTCTCTCACA CTTCCCTAAG CTCCGACTTT TTTCTCCTAG AGCAAGTTAG     2580

CTAAACTGTT TCCCGAGTGC TCAGTCGCAC ACACACCCCC TCCCCAACCC CCAGTATTT      2640

GGTATGGCCC CTCCTGTCCT GTTCAATCAT CTCTGCACTA GAGGTTCCTT GTGCAGAGGG    2700

ATGATGTCCT CCTTGGTGGC TCCTAAGTGT TGCTGTGAGG GGGGTCTATG TTTGCTTGAC    2760

TGGTTGGCTG GATGACCAGT TGAACTGATG CTGGAGGCTA CTGGATGGCT GGGCTAATGC   2820

TGTGAACCAC AGGAGCTACC TAGGAACCCC TTCAACTCAC AGAGGTTCCC CCATCTTCTT    2880

CTGACAGGAA AAACATGGA GTCTATTGGG TTAGGAATGG CCCGGACAGG AGGGATGGTG     2940

GTCATCACAG TGCTGCTGTC TGTGGCCATG TTCCTGTTGG TCGTGGGTCT TATTGTTGCC    3000

CTGCACTGGG ATGCCCGCAA ATGAAAAGGG CTCTCCTGCA TCCCAGGCTC CTCCAAGAAG   3060

TCCAGCCTGC CTCCTGCCAG GCTGTAGTCA CTGGCTTCTC AGTGGCTTTT CTTCCCTCTC   3120

CCCGCCCCCT CCTCGAGTCC ACTCCTGACA GTGCCCCCTC CCTGCTCCCT GTCTCACCTT   3180

GCAGCACTCC CTGCTAGCCC CACTGCAATC CTGCCAACAC TGATTTATCT CTTAACTGTA   3240

CTTAATTCTC ACAATAAAGG CTGACCCACG TAGTATGTCT CATCTCCGAC CATGTCTATG   3300

TGAGTCACCC CTTTAGCTGG TCCCCTTATG CACATATCAA AACTACCAAT GTCAAGGTCA   3360

CGTGCATGTC ATTTTCTCTA TCCCAAACCC CAAGGGTGAC TTTTACCAGG AGGGAGGCAA   3420

GCAGAGGCAG AGATAATGAA GCCTCAAGCC CAGACTAGGG AAGCCCTCCA AGCCCCAGAC   3480

CTAGGGCTTG GGTTTTGCAT CCTGCACTCA GTAGATACCC AAGCAGGAGT CTAGTTGGGC   3540

AGGGGGTAGA AGCTGGATCA CCATGTGAGC CTGACTGGGA AGCTGACAGA ACTAGGGAAG   3600

AACTAGAGAA AACACAAACA GGGCAGGCCC TCCAGCCCTG GGTGAAGAAC ATGCTAAACG   3660

GTTCTAGACC CCTAGAGCCG AGGTGGACGG AAGCTCCTGG AAGGGGGAGG GGGGACACA    3720

ACATAGGTAA ACAGGCAGTG GCACCCTCGT CCATTTTTAA AATATAGTTT TGTTCTATAA  3780

AAGTTTTATT TATTTATTTA TTTGCTTGTT TTTATTTGTT TGTTTGTTTT CCAGAGCTGA  3840

GGCAAAAACC CAGGACCTTG AGCTTGCTAG GCAAGTGCTC TACCACTGAG CTAAATCCCC  3900

AACCCCTGTT TTTGTTTTTT TGAAGCAGGG TTTCTCTGTG TAGCTCTGGC TGTCCTAGAG  3960

CTC                                                                  3963
```

(2) INFORMATION FOR SEQ ID NO:2:

(i) SEQUENCE CHARACTERISTICS:
        (A) LENGTH: 184 amino acids
        (B) TYPE: amino acid (C) STRANDEDNESS: single
           (D) TOPOLOGY: linear (ii) MOLECULE TYPE: protein (xi) SEQUENCE DESCRIPTION: SEQ ID NO:2:

Met Ala Ser Thr Leu Pro Val Gln Thr Leu Pro Leu Ile Leu Ile Leu
1               5                   10                  15

Leu Ala Val Leu Ala Pro Gly Thr Ala Asp Phe Asn Ile Ser Ser Leu
                20                  25                  30

Ser Gly Leu Leu Ser Pro Ala Leu Thr Glu Ser Leu Leu Ile Ala Leu
            35                  40                  45

Pro Pro Cys His Leu Thr Gly Gly Asn Ala Thr Leu Met Val Arg Arg
        50                  55                  60

Ala Asn Asp Ser Lys Val Lys Ser Asp Phe Val Val Pro Pro Cys
65                  70                  75                  80

Arg Gly Arg Arg Glu Leu Val Ser Val Val Asp Ser Gly Ser Gly Tyr
                85                  90                  95

Thr Val Thr Arg Leu Ser Ala Tyr Gln Val Thr Asn Leu Thr Pro Gly
                100                 105                 110

Thr Lys Tyr Tyr Ile Ser Tyr Arg Val Gln Lys Gly Thr Ser Thr Glu
            115                 120                 125

Ser Ser Pro Glu Thr Pro Met Ser Thr Leu Pro Arg Lys Asn Met Glu
        130                 135                 140

Ser Ile Gly Leu Gly Met Ala Arg Thr Gly Gly Met Val Val Ile Thr
145                 150                 155                 160

Val Leu Leu Ser Val Ala Met Phe Leu Leu Val Val Gly Leu Ile Val
                165                 170                 175

Ala Leu His Trp Asp Ala Arg Lys
            180